United States Patent
Brand et al.

(10) Patent No.: US 6,816,745 B1
(45) Date of Patent: Nov. 9, 2004

(54) HOUSING, WITH A TUBULAR CONNECTOR, FOR A HEART STIMULATOR

(75) Inventors: Paul Brand, Järfälla (SE); Rolf Hill, Järfälla (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/830,239

(22) PCT Filed: Oct. 21, 1999

(86) PCT No.: PCT/SE99/01893
§ 371 (c)(1),
(2), (4) Date: Aug. 20, 2001

(87) PCT Pub. No.: WO00/24462
PCT Pub. Date: May 4, 2000

(30) Foreign Application Priority Data

Oct. 27, 1998 (SE) .............................. 9803693

(51) Int. Cl.[7] .............................. A61N 1/372
(52) U.S. Cl. ....................................... 607/37
(58) Field of Search ...................... 607/36–38

(56) References Cited

U.S. PATENT DOCUMENTS

| | | |
|---|---|---|
| 4,262,982 A | 4/1981 | Kenny |
| 4,278,093 A | 7/1981 | Lafortune et al. |
| 4,583,543 A | 4/1986 | Peers-Trevarton |
| 4,934,366 A | 6/1990 | Truex et al. |
| 5,007,864 A | 4/1991 | Stutz, Jr. |
| 5,324,311 A | 6/1994 | Acken |
| 5,383,913 A * | 1/1995 | Schiff .......................... 607/38 |
| 5,545,188 A | 8/1996 | Bradshaw et al. |
| 6,029,089 A * | 2/2000 | Hawkins et al. ............... 607/37 |
| 6,327,502 B1 * | 12/2001 | Johansson et al. ............ 607/36 |

* cited by examiner

*Primary Examiner*—Kennedy Schaetzle
*Assistant Examiner*—Frances P. Oropeza
(74) *Attorney, Agent, or Firm*—Schiff Hardin LLP

(57) ABSTRACT

The present invention relates to a pacer housing (60) comprising a connecter means adapted to receive a connect plug (110) on the proximal end of a lead (15) with an electrode located on the dismal end of said lead, said housing being made of metal, and connecter means comprising a tubular member having two ends and being located inside said housing, a first end (22, 122) of said tubular member being welded or bonded to an opening in a wall of said housing, the second end (23, 123) of said tubular member being closed. Said tubular member comprises a tube (21, 121) made of a metal being weldable or bondable to said metal housing, said tube being structurally intact along its entire length, all interior means (27, 127, 28, 128, 50, 150, 51, 151) in said tube for contacting the contact surfaces (111, 118) on said plug being located within the enclosure formed by said tube, said tube further containing at least one insulating ceramic plug (26, 126) being coaxial with said tube and holding said interior means for contacting said contact surfaces on said plug.

7 Claims, 2 Drawing Sheets

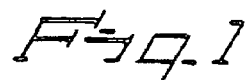
(PRIOR ART)
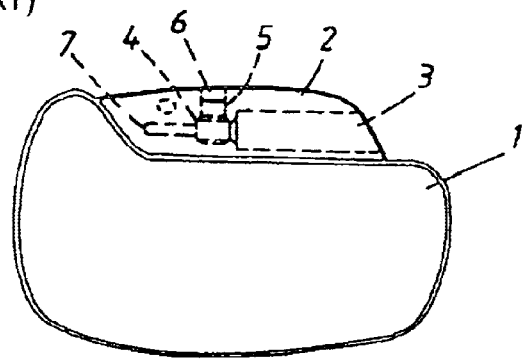
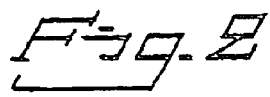
(PRIOR ART)
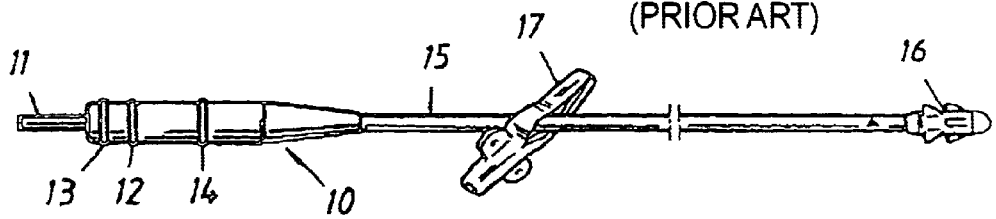
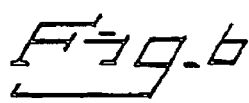
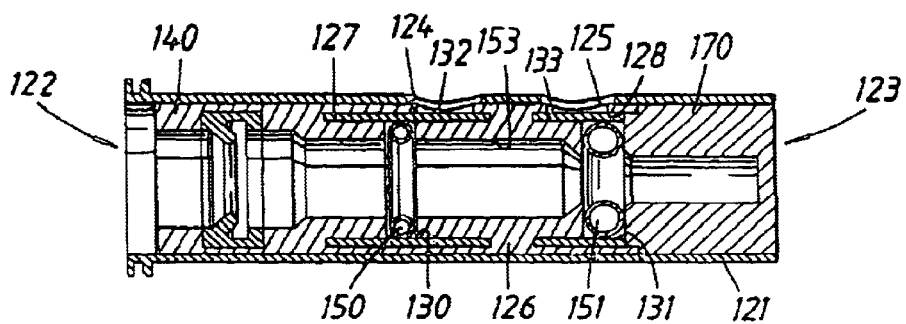

HOUSING, WITH A TUBULAR CONNECTOR, FOR A HEART STIMULATOR

BACKGROUND OF THE INVENTION

1. Field of the Invention

The present invention relates to pacer housings and more particularly to those parts of the housing intended for connection to the electrode leads.

2. Description of the Prior Art

Implantable pacers normally have a pacer housing (also called can) containing electronic circuitry and a unit for electric power as well as different electrodes which are connected to the interior parts in the pacer housing and which are to be implanted in or in the vicinity of the heart. The electrodes are connected to the pacer by means of leads. The internal parts of the pacers have to be well protected against the internal environment, especially the body fluids in the body for a long period of time, which places strict requirements on all entries into the interior of the can and especially on the connections of the leads to the housing. At the same time it should be possible to disconnect the pacer from the implanted leads for replacement or servicing of the pacer. The connective parts of the pacer and the leads have largely been standardized so as to encompass a relatively deep female socket comprising a number of contact surfaces whereas the leads are provided with a male part comprising one or several corresponding peripheral, generally circular contact surfaces.

At present the connective part of the pacer housing containing the female socket is made of a transparent material, normally epoxy resin, which is molded onto the housing and onto contacts extending outwardly from the housing. The male part of the leads is normally locked by means of set-screws, although other fastening means have been envisaged. The positioning and alignment of the different contact surfaces and of the fastening means or metallic threads for the set screws prior to the molding of the connective part is however very complicated and the delay in the manufacturing process incurred by the curing of the epoxy resin is considerable.

It would thus be desirable if the molding procedure could be dispensed with.

It has been discussed that these complexities could be avoided by designing the pacer with a socket located inside the metal housing. This kind of socket, sometimes termed "black holes", is not used at present.

U.S. Pat. Nos 4,934,366 and 5,324,111, the teachings of both of which are incorporated herein by reference, describe two interior sockets or black holes for pacers. Both designs have a tubular member formed by a number of alternating sections made of metal and insulating ceramic, respectively. An end section of metal can be welded or bonded to an opening in the pacer housing by means of a flange. The use of different materials, however, sets high standards in regard of precision and durability of the component parts and as well as on the assembly procedure thereof. This is especially important since the interior sockets must meet very high standards regarding the integrity of the interior of the pacer housing during long times of implantation in a demanding environment. The manufacture of these known sockets thus is relatively complicated. The same is true for the device disclosed in U.S. Pat. No. 4,262,982, a ceramic socket combined with a metal flange for welding to a pacer housing and with a metallic interior contact pin. This device also has locking means in the form of an inwardly directed, circumferential rib located adjacent the opening of socket. This rib is intended to cooperate with barb-shaped sealing rings on the contact plug on the proximal end of the lead or catheter.

SUMMARY OF THE INVENTION

It is an object of the invention to provide a pacer housing which allows the molding procedure to be avoided and the design of an interior socket to be simplified to a high degree while still meeting the required high standards The above object is achieved in accordance with the principles of the present invention in a pacemaker housing having a connector arrangement which is adapted to receive a contact plug at the proximal end of a lead, the pacemaker housing having a housing enclosure made of metal and the connector arrangement forming a tubular member with two opposite ends disposed inside of the housing. A first end of the tubular member is open and is welded or bonded to an opening in the wall of the housing. The second end of the tubular member is closed. The tubular member is made of metal that is weldable or bondable to the metal housing. The tubular member is structurally intact along its entire length. A number of interior components, adapted for mechanical and electrical contact with contact surfaces of the contact plug of the lead, are held in an insulating ceramic plug which is located in the interior of the tubular member and is coaxial therewith.

DESCRIPTION OF THE DRAWINGS

FIG. 1 is a side view of a conventional pacer housing having a transparent molded connector part.

FIG. 2 shows a lead with a male connector plug, of the type used with the inventive pacer housing.

FIG. 6 is a side sectional view of a further embodiment of a connective part constructed in accordance with the principles of the present invention.

DESCRIPTION OF THE PREFERRED EMBODIMENTS

Figure 3:
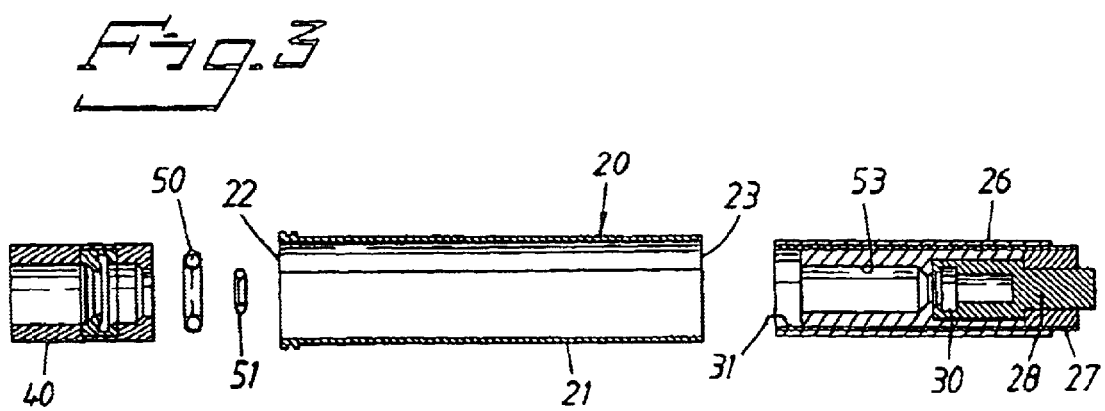
FIG. 3 shows an exploded view of various components of a connective part constructed in accordance with the principles of the present invention.

FIG. 1 illustrates a conventional pacer housing 1 having a molded, transparent connective part 2. The connective part 2 includes a female socket 3. The inner end of the socket 3 is provided with a longitudinal bore 7 having a relatively small diameter. The bore 7 is provided with a contact surface 4 adjacent to which threads for a set or lock screw 5 are located in a bore 6 oriented orthogonally relative to the female socket. The housing 2 is hermetically sealed in relation to the molded part 2 and the contact between the interior electronics and the contact surface 4 is achieved by means of a feed-through. The feed-through is a ceramic plug, typically made of alumina, into which one or more leads have been soldered. This lead is bonded (e.g. ultrasonically welded) to the electronics and to the contact surface 4. The ceramic plug is soldered or brazed with gold into a sleeve made of titanium. This operation may be done at any time before the assembly of the pacer housing 2. The sleeve is welded into an opening in the housing 2 in a sealing manner during the assembly of the pacer housing 2 that normally is formed by two halves. Before the connective part is molded onto the housing, these halves are welded together and sealed.

FIG. 2 illustrates a lead 15 having a proximal connecting plug 10 and a distal, transvenous, intracardial electrode 16 as well as an attachment element 17 for suturing the proximal end of the lead in the body of the patient. The connecting plug 10 is designed to be received in the socket 3 and the end thereof is provided with a longitudinally projecting contact pin 11 as well as a cylindrical body provided with sealing rings 12, 13, 14 intended to engage and seal against the corresponding inner cylindrical surface of the female socket 3. The shape of the pin 11 corresponds to the shape of the bore 7. When the plug 10 is inserted into the socket 3 the pin 11 engages the contact surface 4 and the set-screw in the bore 6 can be tightened against the pin 11 in order to securely lock the plug 10 in the socket 3. The complexities involved in holding the bores, contact surfaces and threads in position and keeping them open and tree from the molding material during the molding process are evident.

For simplicity, the above prior art device has been illustrated as being unipolar. A bipolar embodiment naturally will be more complex to manufacture. The preferred embodiments of the invention described below will relate to bipolar embodiments.

Figure 4:
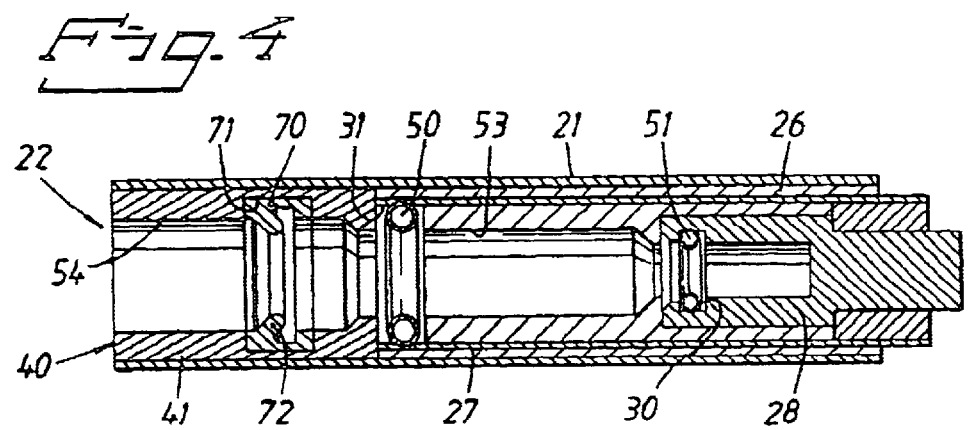
FIG. 4 is a side sectional view of an assembled connective part constructed in accordance with the principles of the present invention.
Figure 5:
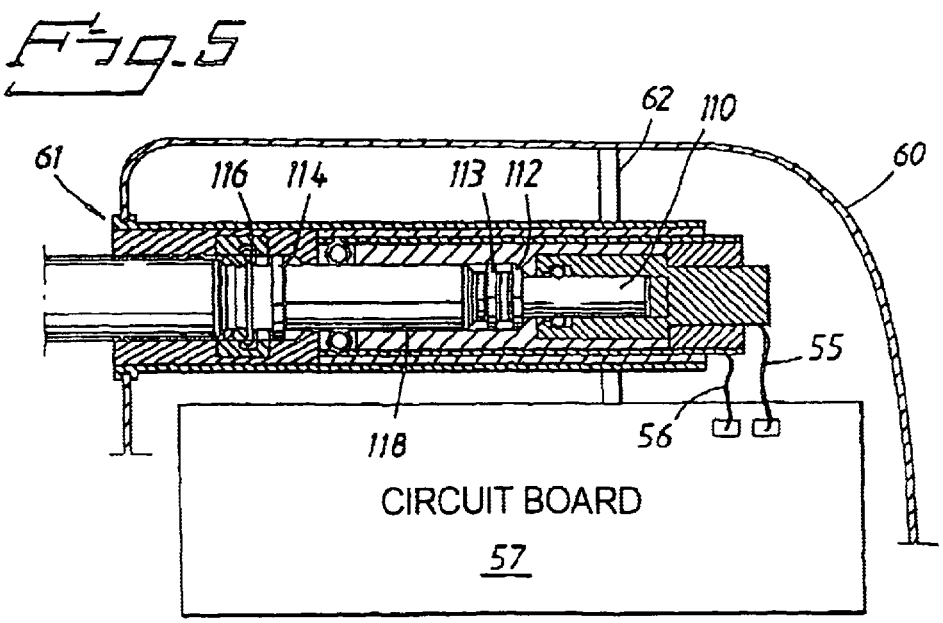
FIG. 5 is a side sectional view of a portion of a pacer housing constructed in accordance with the principles of the present invention with a connector plug of ane electrode lead inserted therein.

FIGS. 3-5 show a preferred embodiment of the invention having a tubular member 20. For clarity, all reference signs have not been repeated throughout all drawings.

The member has a tube 21 with two open ends 22, 23. One end 22 is to be welded into an opening in the pacer housing. The tube 21 is made of the same metal as the pacer housing, in this case titanium. The opposite end 23 of the tube 21 is provided with a ceramic plug 26 fitting snugly in the tube 21 and soldered with for instance gold against the inside of the tube 21. A metallic tubular sleeve 27 serving as a contact sleeve has been molded or bonded into the ceramic plug 26.

The ceramic plug 26 is provided with an interior bore corresponding to the shape of the proximal part of the male connector in the same way as the molded prior art female connector described above and thus includes an interior sealing surface 53 for engagement with the sealing rings on the male connector.

The outer side of the outer end of the contact sleeve 27 is free from ceramic and extends out past the end of the tube 21, thus forming a contact surface for connection to the interior of the housing.

The inner bore of the ceramic plug is closed by a metal plug 20 28 having an inner bore at the inner end sized to correspond to the contact pin of the male connector and forming the innermost part of the inner bore of the ceramic plug. The inner bore of the metal plug 28 also comprises an inner, circumferential groove 30. The outer end of the metal 28 plug extends out from the ceramic, past the end of the contact sleeve 27, thus forming a second contact surface. The metal plug 28 may be molded into the ceramic plug 26 or may be a separate part inserted and bonded into the inner bore of the ceramic plug.

The end part 31 of the inside of the contact sleeve 27 is not covered with the ceramic material. In this way an inner circumferential groove is obtained in the inner bore of the ceramic plug 26. The bottom of the groove consists of the metal in the contact sleeve 27.

Thus, when the ceramic plug 26 has been soldered or bonded into place, the second end 23 will be completely sealed by the plug 26 although allowing electrical connection to the interior of the tube via the contact ring 27 and the metal plug 22. It should be noted that several concentric contact rings in a staggered configuration separated by insulating ceramic material could be used. The number of the connections thus would be limited only by the constraints given by the dimensions.

The manufacturing steps involved in the above can be carried out in advance as desired so as to achieve a prefabricated tube.

The end of the prefabricated tube can be welded to the pacer housing and the housing parts can be welded together after the connection of interior leads from the interior electronics to the contact ring and the plug, should this be desired. The remaining parts, i.e. the means achieving the contact between the contact rings and the contact surfaces on the male connector part on the lead and the means locking or fixating the male connector part in the socket, can easily be inserted afterwards. This means for instance that these parts would not interfere with the standard helium-based procedures for testing the housing with connector for leaks or that these parts would not be affected by the leak testing procedure.

FIG. 3 shows the main components of the tubular member, the tube 21 with the ceramic plug 26, a locking arrangement 40 and two circular spring contacts 50, 51. The spring contacts are similar to the spring contacts used in U.S. Pat. No. 4,934,366.

The locking arrangement 40 is designed in a similar way as the lead locking device disclosed in U.S. Pat. No. 4,262,982, herewith incorporated by reference.

The tube 21 preferably is of the same material as the pacer housing, which normally is made of titanium. The ceramic plug may for instance be made of alumina $Al_{O3}$, and the contact rings may for instance be made of stainless steel or of titanium.

FIG. 4 shows the tubular connective member in an assembled state and FIG. 5 shows the tubular connective member mounted in a pacer housing 60. The male connector plug 110 is shown inserted into the connective member.

The lead locking arrangement 40 has a resilient ring 70 mounted in an interior, circumferential groove 71 in an inner sealing surface 54 in a hollow locking cylinder 41 fitting in the open end of the tube 21. The resilient ring is mounted so as to be located directly behind the hindmost sealing ring 116 on the plug 110. The resilient ring has an inner circumferential locking flange 72 biased inwardly into the central bore. When the plug 110 is inserted into the connective member, the sealing rings 112, 113, 114 and 116 thus will pass the flange and the hindmost sealing ring 116 will be held by the flange 72 against a movement outwardly from the connective member 40. Other lead locking means that could be used in this embodiment are for instance disclosed in U.S. Pat. No. 4,934,366, the teachings of which are incorporated herein by reference.

FIG. 5 shows how the tube has been mounted in a pacer housing 60 and welded to an opening 61 in the housing via flanges located on the outside of the tube ends. FIG. 5 also shows a male connector plug 110 inserted in the tubular member. The plug has a contact pin 111, a contact surface 118 and four sealing rings 112, 113, 114, 116. The sealing rings 112–114, 116 are in engagement with the interior sealing surfaces 53, 54 and the spring contacts are in contact pin 111 respectively with the contact surface 118.

The connector means can be achieved in a simple way compared with the prior art molded connector means.

As mentioned above, the ceramic part can be soldered into the tube in advance by similar methods as used when obtaining the feed-through in the prior art. The tube then is placed in the opening in one of the pacer housing halves and may supported by a support 62 located in the housing, should this prove desirable. The support in this case is a bracket being a part of the inner module in the pacer housing having an opening that is complementary to the outside of the tube. Conductors 55, 56 are bonded (typically by means of ultrasonic welding) to the connecting parts of the an electronic circuit board 57 and to the parts of the contact ring and the metal plug that are accessible at the end of the tube. The housing halves then are assembled and the two halves and the ends of the tube are welded together by means of a laser beam to form a sealed unit. This unit then is tested for leakage, for instance by means of standard helium-based procedures. It should be noted that no other kinds of work operations than those already used in the prior art are necessary.

The pacer then is finished by slipping the resilient spring contacts into the respective interior grooves in the ceramic plug and by inserting and bonding the lead locking means into place in the open end of the tube.

The new connective part thus is very simple to manufacture and to mount in the pacer housing. The welding and sealing of the housing only includes the additional step of welding the ends of the tube to the edges of the openings in the housing, which is performed in the same operation as the welding of the two housing halves. After the welding operation, no further operations are necessary, except for the simple insertion of spring contact rings and lead-locking mechanism.

Since the tube after the welding operation in principle forms an integral part of the pacer housing, a high degree of tightness and integrity is obtained. The tube will ensure a high strength and a high durability of the connective part, whilst the ceramic plug will ensure a high degree of tightness in view of the large contact area between ceramic plug and tube that can used for soldering, i.e. sealing.

One important feature of the invention is the ability to achieve a high capacitance between contact ring and tube. The ring and tube will be separated by the ceramic, which is chosen to be insulating and thus is a dielectricum.

The preferred embodiment naturally has a high capacitance since the contact ring has to extend a long way along the tube. This capacitance of course can be increased if a capacitor is connected in-between the outer tube and the contact ring.

In an alternative embodiment, illustrated in FIG. 6, a tube 121 has opposite ends 122, 123 and the mid-section of the tube 121 is provided with two relatively small lateral openings 124, 125. The openings 124, 125 are sealed by means of a ceramic plug 126 fitting snugly in the tube and soldered with gold or otherwise bonded against the inside of the tube. Two contact rings 127, 128 have been molded into the ceramic plug.

The ceramic plug 126 is provided with an interior bore corresponding to the shape of the proximal part of the male connector in the same way as the molded prior art female connector described above. The ceramic plug thus includes an interior-sealing surface 153 for engagement with sealing rings on the male connector.

The central part of the inside of each of the contact rings is not covered with the ceramic material. In this way two inner circumferential grooves 130, 131 are obtained in the inner bore of the ceramic plug. The bottom of the grooves consists of the metal in the contact rings. Two openings 132, 133 are also provided in the outer surface of the ceramic plug 126 that may be made to coincide with the lateral openings 124, 125 in the tube wall. These openings allow access to the contact rings 127, 128 when the ceramic plug 126 has been mounted correctly in the tube 121. Leads for contacting the interior of the housing can be bonded to the parts of the contact rings 127, 128 accessible through the openings 124, 125 and 132, 133.

Typical dimensions for a tube intended to house a standard IS-1 male connector are for instance an inner diameter of 5 mm, a wall thickness of 0.3 mm (i.e. the same as the thickness of typical pacer housing walls) and a diameter of the holes 124, 125 of about 2 mm. A minimum area of about 4 $mm^2$ is necessary for the equipment presently used for bonding leads to metallic surfaces. The length of the tube is of course adapted to the specific housing into which it is to be placed, but might typically be about 25 mm.

Thus, when the ceramic plug 126 has been soldered or bonded into place, the openings 124, 125 will be completely sealed by the plug 126 although allowing electrical connection between the interior of the tube and the interior of the housing via the contact rings 127,128.

The inner end 123 of the tube 121 is closed by means of a ceramic plug 170 soldered into the tube. The plug 170 may be made in one piece with the plug 126 or, as illustrated, in a separate piece.

The grooves 130, 131 contain spring contact rings 150, 151 of the same type as the ones described in the preferred embodiment described above.

The locking arrangement 140 is located in the same place and are identical to the locking arrangement described in the above preferred embodiment. The locking arrangement therefore is not described in more detail here.

It should be noted that the size of the openings 124, 125 being necessary to allow the bonding of the leads to the parts of the contact rings accessible through the openings 124, 125 and 131, 132 is small, in relation to the entire circumference and to the length of the tube. The openings thus do not affect the structural integrity of the tube. The contact rings 127, 128 moreover overlap the openings and are bonded thereto by means of the intermediate layer of ceramics, in this way strengthening the area in which the openings are located.

Typical dimensions for a tube intended to house a standard IS-1 male connector are for instance an inner diameter of 5 mm, a wall thickness of 0.3 mm (i.e. the same as the thickness of typical pacer housing walls) and a diameter of the holes 124, 125 of about 2 mm. A minimum area of about 4 $mm^2$ is necessary for the equipment presently used for bonding leads to metallic surfaces. The length of the tube is of course adapted to the specific housing into which it is to be placed, but might typically be about 25 mm.

These dimensions of course can be varied as long as the tube remains structurally intact, i.e. as long as the tube has a strength and rigidity that is sufficient to prevent loads, including thermal stresses, on the housing and/or the connector to be transferred as tensile forces to the ceramic parts. Of course, low tensile forces not exceeding the tensile strength of the ceramic could be accepted. Since there are standards regarding the loads a pacer housing and connector should be able to withstand and regarding the overall tightness of the housing, variations of the dimensions only would involve standard stress calculations and dimensioning well within the scope of the man in the art. It should be noted that this also could take the degree of soldering between ceramic plug and tube into account, since this would determine the extent to which tube and ceramic would function as a composite without going outside the ordinary skill of the man skilled in the art.

The number of lateral openings of course only is limited by the length of the tube and by the above considerations regarding the structural integrity.

It should also be noted that the main design features of the above two embodiments could be combined in different ways. One or several of the connections of the above first embodiment thus could be combined with one or several connections according to the above second embodiment. For instance, should it be desired to provide four contact means for a lead with four conductors, two of them could for instance be connected via an end plug designed in accordance with the first embodiment and the other two by means of lateral openings designed in accordance with the second embodiment.

It should also be noted that the ceramic material in the connector partly or entirely could be replaced by another insulating material, for instance a suitable plastics material.

Although modifications and changes may be suggested by those skilled in the art, it is the intention of the inventors to embody within the patent warranted hereon all changes and modifications as reasonably and properly come within the scope of their contribution to the art.

We claim:

1. A pacer housing comprising:

a metallic housing enclosure;

a connector arrangement adapted to receive a contact plug of an electrode lead, said connector arrangement comprising a tubular member disposed inside said housing and having a first end and a second end opposite said first end, said first end of said tubular member being attached, by an attachment selected from the group consisting of a weld and bond, to an opening in a wall of said housing, and said second end of said tubular member being closed;

said tubular member being formed by a tube comprised of a metal attachable to said housing enclosure by said attachment, said tube having a length and being continuous along an entirety of said length;

a plurality of interior elements adapted for mechanical and electrical contact with said contact plug; and an insulating plug in comprised of ceramic material fitted into an interior of said tube and closing said second end of said tubular member and having said interior elements mounted therein, said insulating plug being coaxial with said tube and holding said interior elements at respective positions for producing said mechanical and electrical contact with said contact plug, said insulating plug being attached to said tube by an attachment technique selected from the group consisting of soldering and bonding.

2. A pacer housing as claimed in claim 1 wherein said housing enclosure has a housing interior, and further comprising a metallic tubular sleeve embedded in said ceramic plug and having an end projecting from said ceramic plug exposing an exterior contact surface for providing electrical contact with said housing interior, and said sleeve having an opposite end which is exposed in an interior of said tubular member to produce an inner contact surface adapted for electrical and mechanical contact with said contact plug.

3. A pacer housing as claimed in claim 1 wherein said housing enclosure has an interior, and further comprising a metallic plug embedded in said ceramic plug, said metallic plug having an outer end projecting from said ceramic plug to provide an exterior contact surface for electrical contact with said interior of said housing.

4. A pacer housing as claimed in claim 3 wherein said metallic plug has an inner end opposite to said outer end with a bore therein in communication with an interior of said ceramic plug, and adapted to receive and electrically contact said contact plug.

5. A pacer housing as claimed in claim 1 wherein said housing enclosure has an interior, and wherein said ceramic plug has a contact ring therein having an interior surface adapted for making electrical contact with said contact plug, and a contact surface, and wherein said metal tube has a lateral opening therein exposing said contact surface for establishing electrical contact to said interior of said housing.

6. A pacer housing as claimed in claim 5 wherein said contact ring comprises a metal ring attached to said ceramic plug by an attachment technique selected from molding and bonding, and wherein said ceramic plug has an exterior with an opening therein in registration with said lateral opening in said metal tube allowing access to said ring from an exterior of said tube.

7. A pacer housing as claimed in claim 6 wherein said metal ring has an interior that is free of said ceramic forming a peripheral groove in an interior of said ring allowing access to said ring from said interior of said metal tube.

* * * * *